United States Patent
Kotra et al.

(10) Patent No.: US 11,370,723 B2
(45) Date of Patent: Jun. 28, 2022

(54) PROCESS FOR PREPARING LINEAR ALKYL BENZENE

(71) Applicant: Reliance Industries Limited, Mumbai (IN)

(72) Inventors: Viswanath Kotra, Palava (IN); Pavankumar Aduri, Palava (IN); Vibhuti Dhukande, Pune (IN); Mangesh Raghunath Sakhalkar, Panvel (IN); Uday Meghashyam Ratnaparkhi, Navi Mumbai (IN); Rahul Kumbhar, Pune (IN); Suresh Iyengar, Navi Mumbai (IN); Rahul Mahadeo Dhawade, Nagpur (IN); Romal Chafle, Wardha (IN); Parasuveera Uppara, Navi Mumbai (IN); Gordhan Das Goyal, Mumbai (IN)

(73) Assignee: RELIANCE INDUSTRIES LIMITED, Mumbai (IN)

(*) Notice: Subject to any disclaimer, the term of this patent is extended or adjusted under 35 U.S.C. 154(b) by 0 days.

(21) Appl. No.: 17/312,307

(22) PCT Filed: Dec. 9, 2019

(86) PCT No.: PCT/IB2019/060557
§ 371 (c)(1),
(2) Date: Jun. 9, 2021

(87) PCT Pub. No.: WO2020/121154
PCT Pub. Date: Jun. 18, 2020

(65) Prior Publication Data
US 2022/0033323 A1   Feb. 3, 2022

(30) Foreign Application Priority Data

Dec. 9, 2018   (IN) .............................. 201821021652

(51) Int. Cl.
*C07C 2/66* (2006.01)
*C07C 6/12* (2006.01)
*C07C 7/04* (2006.01)

(52) U.S. Cl.
CPC .................. *C07C 2/66* (2013.01); *C07C 6/12* (2013.01); *C07C 7/04* (2013.01); C07C 2531/18 (2013.01)

(58) Field of Classification Search
CPC .... C07C 2/66; C07C 6/12; C07C 7/04; C07C 2531/18
See application file for complete search history.

(56) References Cited

U.S. PATENT DOCUMENTS

| 2016/0060277 A1* | 3/2016 | Aduri ................... B01J 31/0298 556/64 |
| 2016/0082426 A1* | 3/2016 | Aduri ...................... B01J 31/40 546/348 |

(Continued)

FOREIGN PATENT DOCUMENTS

| WO | 9803454 A1 | 1/1998 |
| WO | 2014178075 A2 | 11/2014 |

(Continued)

OTHER PUBLICATIONS

International Search Report issued in International Application No. PCT/IB2019/060557 dated Feb. 5, 2020 (3 pages).

(Continued)

*Primary Examiner* — Thuan D Dang
(74) *Attorney, Agent, or Firm* — Osha Bergman Watanabe & Burton LLP

(57) ABSTRACT

The present disclosure relates to a process for preparing linear alkyl benzne (LAB). The process comprises alkylation of benzene with an alkylating agent in the presence of an ionic liquid to obtain a first product mixture comprising a first organic phase and a first aqueous phase comprising (Continued)

Figure 1:
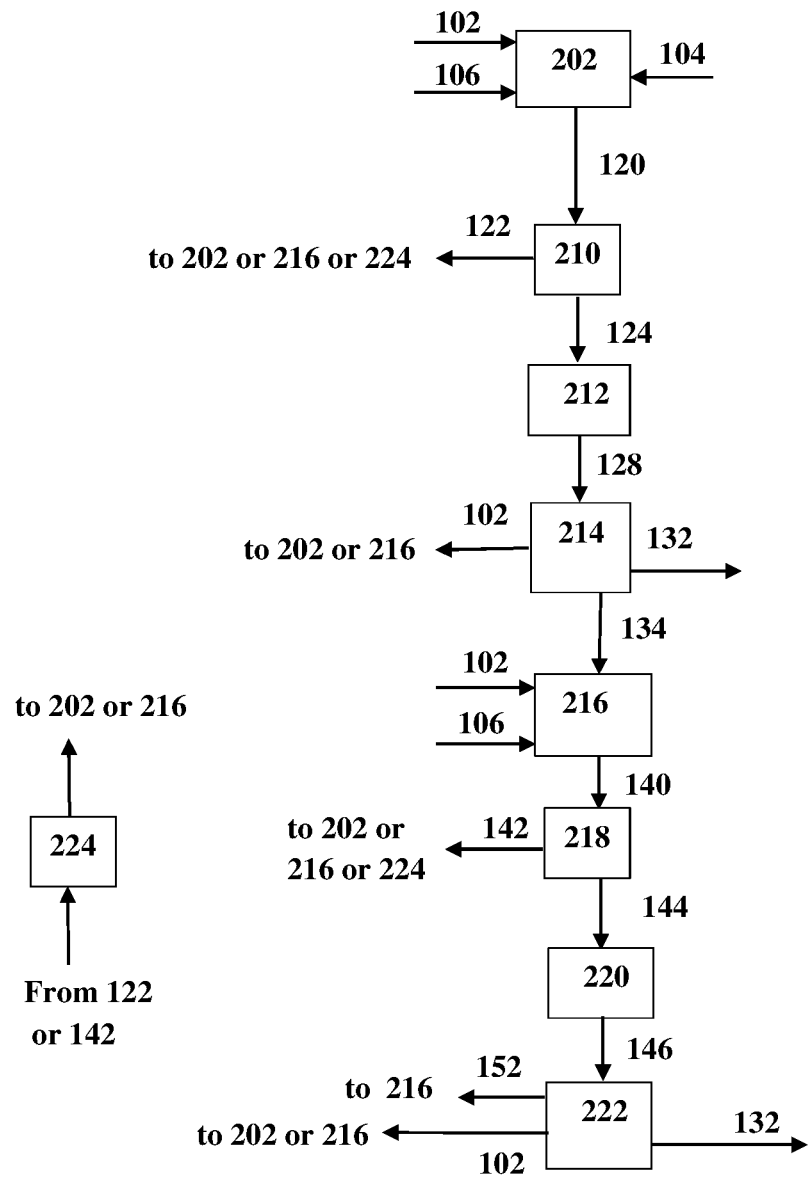

first partially spent ionic liquid. The first organic phase is deacidified and fractionally distilled to obtain a fraction comprising LAB and a fraction comprising HAB. The fraction comprising HAB is transalkylated with benzene in the presence of the ionic liquid to obtain a second product mixture comprising a second organic phase comprising LAB and a second aqueous phase comprising second partially spent ionic liquid. The partially spent ionic liquids are regenerated, and reused in the steps of alkylation or transalkylation for at least 6 cycles.

15 Claims, 2 Drawing Sheets

(56) References Cited

U.S. PATENT DOCUMENTS

| | | | | |
|---|---|---|---|---|
| 2017/0182485 | A1* | 6/2017 | Uppara | B01J 31/0249 |
| 2017/0197994 | A1* | 7/2017 | Yadav | B01J 31/4092 |

FOREIGN PATENT DOCUMENTS

| | | | |
|---|---|---|---|
| WO | 2016005920 | A2 | 1/2016 |
| WO | 2016005952 | A1 | 1/2016 |
| WO | 2016071871 | A1 | 5/2016 |

OTHER PUBLICATIONS

Written Opinion issued in International Application No. PCT/IB2019/060557 dated Feb. 5, 2020 (6 pages).

* cited by examiner

PROCESS FOR PREPARING LINEAR ALKYL BENZENE

FIELD

The present disclosure relates to a process for preparing linear alkyl benzne (LAB).

BACKGROUND

Linear alkyl benzenes (LABs) are important raw materials for various commercial products such as detergent, and surfactants. Commercially, LABs are produced by alkylation of benzene.

Conventionally, the process for the alkylation of benzene is carried out at a high temperature and using an acidic catalyst such as hydrogen fluoride (HF).

HF is a liquid, and it is used as a homogeneous catalyst for the alkylation of benzene. However, HF is highly corrosive in nature and it liberates toxic vapors. Therefore, HF catalyzed processes are associated with drawbakcs such as safety, toxicity, and waste disposal problems. Further, it is difficult to handle HF and recycle it.

Due to the above mentioned drawbacks of HF catalyzed processes, there is a need to develop processes using catalysts other than HF for the alkylation of benzene. Certain catalysts useful for alkylation of benzene are solid in nature and are not soluble in benzene. Such solid and heterogeneous catalyst cannot be retrofitted into a commercial plant that is designed for handling HF, which is a liquid and a homogeneous catalyst. Further, the solid alkylation catalysts can cause fouling of reactors.

Therefore, there is felt a need to develop a process for alkylation of benzene using a catalyst that is safe, easy to regenerate and recycle. Further, it is desired that the process for alkylation of benzene using the catalyst can be retrofitted in the production unit that uses HF for the alkylation of benzene.

OBJECTS

Some of the objects of the present disclosure, which at least one embodiment herein satisfies, are as follows:

An object of the present disclosure is to ameliorate one or more problems of the prior art or to at least provide a useful alternative.

Another object of the present disclosure is to provide a process for alkylation of benzene.

Yet another object of the present disclosure is to provide a process for alkylation of benzene using a catalyst that is safe, easy to regenerate and recycle.

Still another object of the present disclosure is to provide a process for alkylation of benzene that can be retrofitted in an equipment designed for HF-catalyzed alkylation of benzene.

Other objects and advantages of the present disclosure will be more apparent from the following description, which is not intended to limit the scope of the present disclosure.

SUMMARY

In one aspect, the present disclosure provides a process for preparing linear alkyl benzene by alkylation of benzene. The process comprises the following steps.

Benzene is alkylated with an alkylating agent in the presence of an ionic liquid to obtain a first product mixture.

The first product mixture is allowed to settle to obtain a first biphasic mixture comprising a first organic phase and a first aqueous phase. The first organic phase comprises linear alkyl benzene (LAB), heavier alkyl benzene (HAB) and unreacted benzene, and the first aqueous phase comprises first partially spent ionic liquid.

The first organic phase is deacidified to obtain a deacidified first organic phase.

The deacidified first organic phase is fractionally disitlled to obtain a fraction comprising unreacted benzene, a fraction comprising LAB and a fraction comprising HAB.

The fraction comprising HAB is transalkylated with benzene in the presence of the ionic liquid at a temperature in the range of 70° C. to 120° C. to obtain a second product mixture.

The second product mixture is allowed to settle to obtain a second biphasic mixture comprising a second organic phase and a second aqueous phase; wherein the second organic phase comprises LAB and the second aqueous phase comprises second partially spent ionic liquid.

The second organic phase is deacidified to obtain a deacidified second organic phase. The deacidified second organic phase is fractionally distilling to obtain a fraction comprising LAB and a fraction comprising unreacted HAB.

The first partially spent ionic liquid obtained in the alkylation step and the second partially spent ionic liquid obtained in the transalkylation step are regenerated, and the regenerated ionic liquid is reused in the steps of alkylation and/or transalkylation for at least 6 cycles of regeneration.

In accordance with the embodiments of the process of the present disclosure, the ionic liquid used in the alkylation step and the translakylation step is at least one selected from fresh ionic liquid, regenerated ionic liquid, the first partially spent ionic liquid and the second partially spent ionic liquid.

The alkylating agent is at least one olefin selected from the group consisting of C10 to C14 olefins.

In accordance with one embodiment of the process of the present disclosure, the alkylating agent is a hydrocarbon comprising paraffins and olefins. The volume ratio of paraffins to olefins in the hydrocarbon is in the range of 20:1 to 4:1, preferably 7:1 to 15:1.

The mole ratio of benzene to the alkylating agent is in the range of 3:1 to 20:1, preferably 8:1 to 12:1.

In accordance with an embodiment of the present disclosure, the alkylation step is carried out in two stages, wherein the first stage comprises alkylating benzene with a first portion of the alkylating agent to obtain a first resultant mixture comprising unreacted benzene, and the second stage comprises alkylating the first resultant mixture comprising unreacted benzene with a second portion of the alkylating agent to obtain the first product mixture.

The alkylation step is carried out at a temperature in the range of 5° C. to 150° C., preferably at 10° C. to 100° C.

The alkylation step is carried out at a pressure in the range of 1 atmosphere to 50 atmosphere, preferably at 1 atmosphere to 10 atmosphere.

The volume ratio of the ionic liquid to benzene is in the range of 1:1000 to 1:10.

The ionic liquid is a metal halide based ionic liquid obtained by mixing an acidic component with a basic component, wherein the acidic component is a metal halide and the basic component is at least one selected from the group consisting of $(NR_1R_2R_3)_iM_1X_j$, $M_1(OH)_m$, $M_iX_j$, and $BMIMX_i$, wherein M₁ and Mᵢ are metals independently selected from the group consisting of Al, Fe, Zn, Cu, Ni, Ga, Ge and In;

'BMIM' represents 1-Butyl-3-methylimidazolium; and $X_j$ and $X_i$ are halogens independently selected from the group consisting of fluorine, chlorine, bromine and iodine.

In accordance with an embodiment of the process of the present disclosure, the ionic liquid is represented by formula (I), $$[(NR_1R_2R_3)_iM_1]^{n+}[(M_2Y_k)_LX_j]^{n-} \qquad \text{Formula (I)}$$

wherein, $NR_1R_2R_3$ represents an amine, wherein $R_1$, $R_2$ and $R_3$ are independently selected from the group consisting of alkyl, aryl and H;

$M_1$ and $M_2$ are metals independently selected from the group consisting of Al, Fe, Zn, Cu, Ni, Ga, Ge and In;

X and Y are halogens independently selected from the group consisting of fluorine, chlorine, bromine and iodine;

'n' represents 1 to 4, T represents 1 to 6, T represents 1 to 4, 'k' represents 1 to 4, represents 1 to 7, $M_1=M_2$ or $M_1 \neq M_2$, and X≠Y or X≠Y.

The ionic liquid represented by Formula I is prepared by mixing a metal halide of formula $M_2Y_k$ with a basic component of the formula $(NR_1R_2R_3)_iM_1X_j$.

In accordance with another embodiment of the process of the present disclosure, the ionic liquid is represented by formula (II), $$[(M_1)_p(M_2)_q(M_3)_r(OH)_m(X)_n(Y)_o \text{ (first fluid medium)}] \qquad (II)$$

wherein, $M_1$, $M_2$ and $M_3$ are metals independently selected from the group consisting of Al, Fe, Ni, Cu, Zn, Ga, Ge, and In.

X and Y are halogens independently selected from the group consisting of fluorine, chlorine, bromine and iodine;

'p' represents 0 to 5, 'q' represents 0 to 5, 'r' represents 0 to 5, 'm' represents 10 to 420, 'n' represents 10 to 920, 'o' represents 10 to 420, X=Y or OH is hydroxyl group, the first fluid medium is at least one selected from the group consisting of benzene and toluene; wherein the weight % of the first fluid medium in the ionic liquid of formula II is in the range of 10% to 60%.

The ionic liquid represented by Formula II is prepared by mixing metal halides of formula $M_2(X)_n$ and $M_3(Y)_o$ with a basic component of the formula $M_1(OH)_m$.

In accordance with yet another embodiment of the process of the present disclosure, the ionic liquid is represented by formula (III), $$[UM_iX_j]S \qquad \text{Formula (III)}$$

wherein, 'U' represents urea; $M_iX_j$ represents metal halide; wherein M is at least one metal selected from the group consisting of Al, Fe, Zn, Ge, Cu, Ni, In, and Ga; and X is at least one halogen selected from the group consisting of fluorine, chlorine, bromine and iodine;

'i' represents 1 to 6, 'j' represents 1 to 6;

'S' represents a second fluid medium selected from the group consisting of benzene, and toluene; wherein the weight % of the second fluid medium in the ionic liquid of formula III is in the range of 10 to 60%.

The ionic liquid represented by Formula III is prepared by mixing a metal halide of formula $M_iX_j$ with urea as a basic component.

In accordance with still another embodiment of the process of the present disclosure, the ionic liquid is represented by formula (IV), $$[BMIM][(MX_iY_j)_k] \qquad \text{Formula (IV)}$$

wherein, 'BMIM' represents 1-Butyl-3-methylimidazolium, M is at least one metal selected from the group consisting of Al, Fe, Ni, Cu, Zn, Ga, Ge, and In;

X and Y are halogens independently selected from the group consisting of chloride, bromide, fluoride and iodide;

'i' represents 1 to 4, T represents 1 to 4, X=Y or X≠Y;

the ionic liquid of formula IV is optionally mixed with a third fluid medium selected from the group consisting of benzeneand toluene, wherein the weight % of the third fluid medium and the ionic liquid of formula IV is in the range of 10 to 40%.

The ionic liquid represented by Formula IV is prepared by mixing the metal halide of formula) $X_iY_j$ with the basic component of the formula $BMIMX_i$.

In accordance with an embodiment of the process of the present disclosure, the step of regeneration of partially spent ionic liquid involves the following sub-steps.

The first partially spent ionic liquid obtained in the alkylation step and/or the second partially spent ionic liquid obtained in the transalkylation step are mixed with a fourth fluid medium and an alkali followed by stiffing the resultant mixture to obtain a suspension comprising a solid phase and a liquid phase.

The solid phase is separated from the suspension. The separated solid phase is mixed with a metal halide to obtain regenerated ionic liquid.

The alkali is at least on selected from the group consisting of triethylamine, sodium carbonate, sodium bicarbonate, potassium carbonate, potassium bicarbonate, sodium hydroxide and potassium hydroxide.

The separated solid is at least one basic component of ionic liquid selected from the group consisting of $NR_1R_2R_3$, $(NR_1R_2R_3)_iM_iX_j$, $M_1OH$, and $BMIMX_1$.

The fourth fluid medium is at least one selected from the group consisting of ethyl acetate, methyl acetate and water. The step of separating solid phase from the suspension comprises extracting the separated solid using a fifth fluid medium to obtain an extract; and removing the fifth fluid medium from the extract to obtain a residue comprising the solid phase.

The fifth fluid medium is dichloromethane.

In accordance with another embodiment of the process of the present disclosure, the step of regeneration of partially spent ionic liquid involves the following sub-steps.

The first partially spent ionic liquid obtained in the alkylation step and/or the second partially spent ionic liquid obtained in the transalkylation step are mixed with at least one sixth fluid medium and at least one coordinating agent to obtain a suspension comprising an adduct of the coordinating agent with the ionic liquid. The adduct is separated from the suspension. The separated adduct is thermally treated to obtain regenerated ionic liquid. The coordinating agent is at least one selected from the group consisting of secondary alcohol, aromatic alcohol, phenol and ketone. The secondary alcohol is at least one selected from the group consisting of isopropanol and 2-butanol, preferably isopropanol. The aromatic alcohol is 1-phenylethanol. The ketone is acetone.

The molar ratio of the coordinating agent to the liquid ranges from 1:1 to 1:18, preferably 1:3 to 1:6.

BRIEF DESCRIPTION OF THE ACCOMPANYING DRAWING

Figure 2:
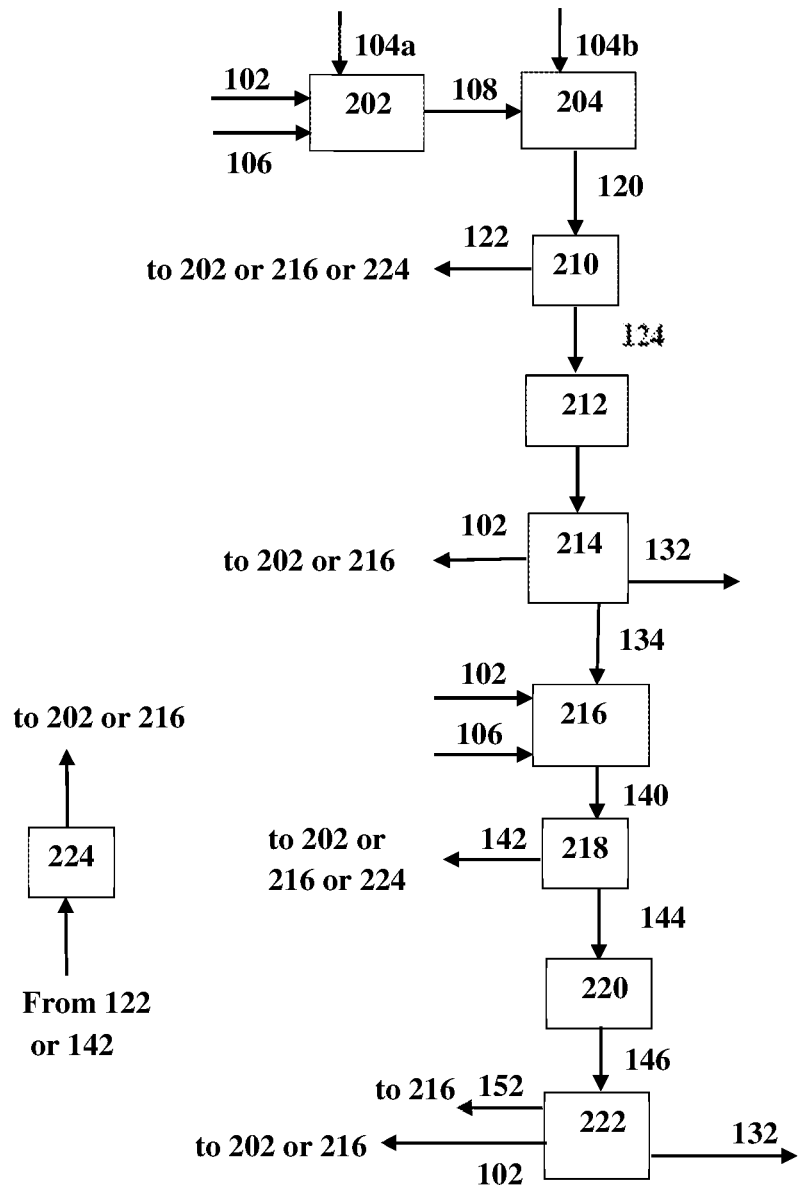

The present disclosure will now be described with the help of the accompanying drawing, in which FIG. 1 illustrates a scheme for preparing LAB using the process of the present disclosure, wherein alkylation is carried out in a single stage; and FIG. 2 illustrates a scheme for preparing LAB using the process of the present disclosure, wherein alkylation is carried out in two stages.

DETAILED DESCRIPTION

Linear alkyl benzenes (LABs) are commercially useful compounds. The conventional processes for preparation of LAB use hydrogen fluoride (HF) which is corrosive and generates toxic fumes. HF is difficult to handle and is difficult to dispose due to its toxicity.

The present disclosure envisages a process of alkylation of benzene that uses a catalyst which is safe, easy to regenerate and recycle.

In one aspect, the present disclosure provides a process for preparing linear alkyl benzene by alkylation of benzene. The process comprises the following steps.

Benzene is alkylated with an alkylating agent in the presence of an ionic liquid as a catalyst to obtain a first product mixture.

The ionic liquid used as a catalyst in the process of the present disclosure is safe, non-corrosive and does not generate toxic fumes.

The alkylating agent is at least one olefin selected from the group consisting of C10 to C14 olefins.

In accordance with one embodiment of the process of the present disclosure, the alkylating agent is a hydrocarbon comprising paraffins and olefins. The volume ratio of paraffins to olefins in the hydrocarbon is in the range of 20:1 to 4:1, preferably 7:1 to 15:1.

The first product mixture obtained in the alkylation step is allowed to settle to obtain a first biphasic mixture comprising a first organic phase and a first aqueous phase. The first organic phase comprises linear alkyl benzene (LAB), heavier alkyl benzene (HAB) and unreacted benzene. The first aqueous phase comprises first partially spent ionic liquid.

The first organic phase is separated and deacidified to obtain a deacidified first organic phase. The deacidified first organic phase is fractionally distilled to obtain a fraction comprising unreacted benzene, a fraction comprising LAB and a fraction comprising HAB.

The fraction comprising HAB is transalkylated with benzene in the presence of the ionic liquid at a temperature in the range of 70° C. to 120° C. to obtain a second product mixture. The second product mixture is allowed to settle to obtain a second biphasic mixture comprising a second organic phase and a second aqueous phase. The second organic phase comprises LAB and the second aqueous phase comprises second partially spent ionic liquid.

The second product mixture obtained in the transalkylation step is allowed to settle to obtain a second biphasic mixture comprising a second organic phase and a second aqueous phase.

The second organic phase is separated and deacidified to obtain a deacidified second organic phase. The deacidified second organic phase is fractionally distilled to obtain a fraction comprising LAB and a fraction comprising unreacted HAB.

The first partially spent ionic liquid obtained in the alkylation step and/or the second partially spent ionic liquid obtained in the transalkylation step are regenerated, and the regenerated ionic liquid is reused in the steps of alkylation or transalkylation for at least 6 cycles of regeneration.

In accordance with the embodiments of the process of the present disclosure, the ionic liquid used in the alkylation step and the translakylation step is at least one selected from the group consisting of fresh ionic liquid, regenerated ionic liquid, the first partially spent ionic liquid and the second partially spent ionic liquid.

The mole ratio of benzene to the alkylating agent is in the range of 3:1 to 20:1, preferably 8:1 to 12:1.

The alkylation step is carried out in a single stage or in two stages, as illustrated in FIG. 1 and FIG. 2, respectively.

In accordance with one embodiment of the present disclosure, the alkylation step is carried out in two stages, wherein the first stage comprises alkylating benzene with a first portion of the alkylating agent to obtain a first resultant mixture comprising unreacted benzene, and the second stage comprises alkylating the first resultant mixture comprising unreacted benzene with a second portion of the alkylating agent to obtain the first product mixture.

It is observed that, when the alkylation step is carried out in two stages, the amount of LAB formed is higher and consequently the amount of HAB formed is lower, as compared to the alkylation step being carried out in a single stage.

The alkylation step is carried out at a temperature in the range of 5° C. to 150° C., preferably at 10° C. to 100° C.

The alkylation step is carried out at a pressure in the range of 1 atmosphere to 50 atmosphere, preferably at 1 atmosphere to 10 atmosphere.

The volume ratio of the ionic liquid to benzene is in the range of 1:1000 to 1:10.

The ionic liquid is a metal halide based ionic liquid obtained by mixing an acidic component with a basic component. The acidic component is a metal halide and the basic component is at least one selected from the group consisting of $(NR_1R_2R_3)_iM_1X_j$, $M_i(OH)_m$, $M_iX_j$, and $BMIMX_j$, wherein $M_1$ and $M_i$ are metals independently selected from the group consisting of Al, Fe, Zn, Cu, Ni, Ga, Ge and In; 'BMIM' represents 1-Butyl-3-methylimidazolium; and $X_j$ and $X_i$ are halogens independently selected from the group consisting of fluorine, chlorine, bromine and iodine.

The ionic liquids used in the process of the present disclosure dissolve in benzene, which is one of the starting materials. Due to their solubility, the ionic liquids are homogeneous catalysts. As a result, the process for alkylation of benzene using the ionic liquids of the present disclosure retrofits into the conventional equipment used for the process for alkylation of benzene using HF as a catalyst, without any significant change in the process equipment.

In accordance with an embodiment of the process of the present disclosure, the ionic liquid is represented by formula (I), $$[(NR_1R_2R_3)_iM_1]^{n+}[(M_2Y_k)_LX_j]^{n-} \qquad \text{Formula (I)}$$

wherein, $NR_1R_2R_3$ represents an amine, wherein $R_1$, $R_2$ and $R_3$ are independently selected from the group consisting of alkyl, aryl and H;

$M_1$ and $M_2$ are metals independently selected from the group consisting of Al, Fe, Zn, Cu, Ni, Ga, Ge, and In.

X and Y are halogens independently selected from the group consisting of fluorine, chlorine, bromine and iodine;

'n' represents 1 to 4, T represents 1 to 6, T represents 1 to 4, 'k' represents 1 to 4, represents 1 to 7, $M_1=M_2$ or $M_1 \neq M_2$, and $X=Y$ or $X \neq Y$.

The ionic liquid represented by Formula I is prepared by mixing a metal halide of formula $M_2Y_k$ with a basic component of the formula $(NR_1R_2R_3)_iM_1X_j$.

In accordance with another embodiment of the process of the present disclosure, the ionic liquid is represented by formula (II),

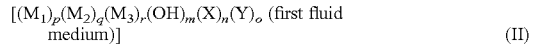

$$[(M_1)_p(M_2)_q(M_3)_r(OH)_m(X)_n(Y)_o \text{ (first fluid medium)}] \quad\quad (II)$$

wherein, $M_1$, $M_2$ and $M_3$ are metals independently selected from the group consisting of Al, Fe, Ni, Cu, Zn, Ga, Ge, and In;

X and Y are halogens independently selected from the group consisting of fluorine, chlorine, bromine and iodine;

'p' represents 0 to 5, 'q' represents 0 to 5, 'r' represents 0 to 5, 'm' represents 10 to 420, 'n' represents 10 to 920, 'o' represents 10 to 420, $X=Y$ or OH is hydroxyl group, the first fluid medium is at least one selected from the group consisting of benzene and toluene; wherein the weight % of the first fluid medium in the ionic liquid of formula II is in the range of 10% to 60%.

The ionic liquid represented by Formula II is prepared by mixing metal halides of formula $M_2(X)_n$ and $M_3(Y)_o$ with a basic component of the formula $M_i(OH)_m$.

In accordance with yet another embodiment of the process of the present disclosure, the ionic liquid is represented by formula (III),

$$[UM_iX_j]S \quad\quad \text{Formula (III)}$$

wherein, 'U' represents urea; $M_iX_j$ represents metal halide, wherein M is at least one metal selected from the group consisting of Al, Fe, Zn, Ge, Cu, Ni, In, and Ga; and X is at least one halogen selected from the group consisting of fluorine, chlorine, bromine and iodine;

'i' represents 1 to 6, 'j' represents 1 to 6;

'S' represents a second fluid medium selected from the group consisting of benzene, and toluene; wherein the weight % of the second fluid medium in the ionic liquid of formula III is in the range of 10 to 60%.

The ionic liquid represented by Formula III is prepared by mixing a metal halide of formula $M_iX_j$ with urea as a basic component.

In accordance with still another embodiment of the process of the present disclosure, the ionic liquid is represented by formula (IV),

$$[BMIM][MX_iY_j)_k] \quad\quad \text{Formula (IV)}$$

wherein, 'BMIM' represents 1-Butyl-3-methylimidazolium;

M is at least one metal selected from the group consisting of Al, Fe, Ni, Cu, Zn, Ga, Ge, and In;

X and Y are halogens independently selected from the group consisting of chloride, bromide, fluoride and iodide;

'i' represents 1 to 4, T represents 1 to 4, $X=Y$ or $X \neq Y$;

the ionic liquid of formula IV is optionally mixed with a third fluid medium selected from the group consisting of benzene, and toluene, wherein the weight % of the third fluid medium and the ionic liquid of formula IV is in the range of 10% to 40%.

The ionic liquid represented by Formula IV is prepared by mixing the metal halide of formula $MY_j$ with the basic component of the formula $BMIMX_i$.

In accordance with an embodiment of the process of the present disclosure, the step of regeneration of partially spent ionic liquid involves the following sub-steps.

The first partially spent ionic liquid obtained in the alkylation step and the second partially spent ionic liquid obtained in the transalkylation step are mixed with a fourth fluid medium and an alkali followed by stirring the resultant mixture to obtain a suspension comprising a solid phase and a liquid phase.

The solid phase is separated from the suspension. The separated solid phase is mixed with a metal halide to obtain regenerated ionic liquid.

The alkali is at least on selected from the group consisting of triethylamine, sodium carbonate, sodium bicarbonate, potassium carbonate, potassium bicarbonate, sodium hydroxide, and potassium hydroxide.

The separated solid is at least one basic component of ionic liquid selected from the group consisting of $NR_1R_2R_3$, $(NR_1R_2R_3)_iM_iX_j$, $M_1OH$, and $BMIMX_i$.

The fourth fluid medium is at least one selected from the group consisting of ethyl acetate, water, and methyl acetate.

In accordance with an embodiment of the present disclosure, the step of separating solid phase from the suspension comprises extracting the separated solid using a fifth fluid medium to obtain an extract; and removing the fifth fluid medium from the extract to obtain a residue comprising the solid phase.

The fifth fluid medium is dichloromethane.

In accordance with another embodiment of the process of the present disclosure, the step of regeneration of partially spent ionic liquid involves the following sub-steps.

The first partially spent ionic liquid obtained in the alkylation step and the second partially spent ionic liquid obtained in the transalkylation step are mixed with at least one sixth fluid medium and at least one coordinating agent to obtain a suspension comprising an adduct of the coordinating agent with the ionic liquid.

The adduct is separated from the suspension. The separated adduct is thermally treated to obtain regenerated ionic liquid.

The coordinating agent is at least one selected from the group consisting of secondary alcohol, aromatic alcohol, phenol and ketone. The secondary alcohol is at least one selected from the group consisting of isopropanol and 2-butanol, preferably isopropanol. The aromatic alcohol is 1-phenylethanol. The ketone is acetone.

The molar ratio of the coordinatingagent to the metal halide of the ionic liquid ranges from 1:1 to 1:18, preferably 1:3 to 1:6.

The ionic liquid used in the process of the present disclosure is easily regenerated, and the generated ionic liquid can be used in alkylation and/or transalkylation steps of the present disclosure for at least 6 cycles of regeneration. After a number of regeneration cycles, spent ionic liquid is obtained. Tar and conjunct polymer are the major impurities present in the spent ionic liquid.

The spent ionic liquid is easily disposed after separating the spent ionic liquid from tar and the conjuct polymer. The disposal of spent ionic liquid comprises the following sub-steps.

The spent ionic liquid is dissolved with at least one seventh fluid medium to obtain a spent ionic liquid solution. The seventh fluid medium is capable of dissolving tar and the conjunct polymer. Water is added to the spent ionic liquid solution and the resultant mixture is stirred to obtain a suspension. The suspension is filtered to obtain a residue and a filtrate. The residue is dried. The seventh fluid medium is recovered from the filtrate. The residue is sent for effluent treatment.

The seventh fluid medium is at least one selected from the group consisting of aldehydes, ketones, and esters.

FIGS. 1 and 2 depict a schematic representation of the process of preparing the linear alkyl benzene of the present disclosure.

FIG. 1 depicts the preparation of linear alkyl benzene by alkylation of benzene, wherein alkylation is carried out in a single stage. The first step is alkylation of benzene with an alkylating agent in the presence of an ionic liquid. Benzene (102), an alkylating agent (104) and an ionic liquid (106) are fed to the first reactor (202). For the alkylation step, benzene (102) can be fresh benzene or recovered benzene or combination thereof. The ionic liquid (106) can be fresh ionic liquid or recycled ionic liquid or regenerated ionic liquid or combination thereof.

The first product mixture (120) from the reactor is fed to a first settler (210). A first biphasic mixture is formed in the first settler (210). The first aqueous phase (122) is either transferred to the first reactor (202) or a second reactor (216) or is sent for catalyst recovery unit (224). The first organic phase (124) is transferred to a first purifier (212). In the first purifier (212), the first organic phase is deacidified. The deacidified first organic phase (128) is transferred to a first fractionating column (214).

The step of fractionation provides a fraction comprising unreacted benzene (102), a fraction comprising LAB (132) and a fraction comprising HAB (134). Unreacted benzene (102) can be recycled to the first reactor (202) or the second reactor (216).

The next step is transalkylation of HAB (134) with benzene (102) and ionic liquid (106) in a second reactor (216) to obtain a second product mixture (140).

For the transalkylation step, the benzene (102) can be fresh benzene or recovered benzene or combination thereof. The ionic liquid (106) can be fresh ionic liquid or recycled ionic liquid or regenerated ionic liquid or combination thereof.

The second product mixture (140) is transferred to a second settler (218). A second biphasic mixture is formed in the second settler (218). The second aqueous phase (142) is either transferred to the first reactor (202) or the second reactor (216) or is sent to the catalyst recovery unit (224). The second organic phase (144) is transferred to a second purifier (220). In the second purifier, the second organic phase is decidified. The deacidified second organic phase (146) is transferred to a second fractionating column (222). The step of fractionation provides a fraction comprising unreacted benzene (102), a fraction comprising LAB (132) and a fraction comprising unreacted HAB (152).

Unreacted HAB (152) obtained from the second fractionating column (222) is transferred to a second reactor (216) for transalkylation.

Unreacted benzene fractions obtained from the first fractionating column (214) and the second fractionating column (222) can be recycled to the first reactor (202) and/or to the second reactor (216). The first aqueous phase (122) and the second aqueous phase (142) can be either transferred to the first reactor (202) or the second reactor (216) or are sent for catalyst recovery (224).

FIG. 2 depicts preparation linear alkyl benzene by alkylation of benzene, wherein the alkylation is carried out in two stages. The first stage of alkylation takes place in first reactor (202) and the second stage of alkylation takes place in a third reactor (204). The alkylating agent is divided into two portions. The first portion of the alkylating agent (104a) is fed to the first reactor (202). The first resultant mixture mixture (108) obtained from the first reactor (202) is fed to the third reactor (204). The third reactor (204) is fed the second portion of the alkylating agent (104b). The first product mixture (120) obtained from the third reactor (204) is fed to the first settler (210). The rest of the process is similar to the process described in FIG. 1.

The present disclosure is further described in light of the following laboratory scale experiments which are set forth for illustration purpose only and not to be construed for limiting the scope of the disclosure. These laboratory scale experiments can be scaled up to industrial/commercial scale and the results obtained can be extrapolated to industrial/commercial scale.

Experimental Details

EXAMPLE-1

Experiment 1: Alkylation Reaction

225 Litre/h (194 kg/h) of benzene and 3 liter/h of freshly prepared ionic liquid as catalyst $[N(C_2H_5)_3\text{-}Al]^+[Al_2Cl_7]^-{}_3$ were mixed in a first static reactor. Benzene was alkylated by contacting the mixture with 425 litre/h of an alkylating agent containing 12% C10-C14 olefins and 88% C10-C14 paraffins at 50° C. in a first reactor obtain a first product mixture.

The first product mixture from the first reactor was sent to a settler (vertical two stage separator) to obtain a first biphasic mixture comprising a first organic phase and a first aqueous phase. The first organic phase comprised linear alkyl benzene (LAB), heavier alkyl benzene (HAB) and unreacted benzene, and the first aqueous phase comprised first partially spent ionic liquid.

The first organic phase was analyzed for olefin content, and it was observed that the conversion of olefin obtained was 99.7%. The presence of linear alkyl benzene in the first organic phase formation was confirmed by gas chromatography (GC).

The top hydrocarbon layer was collected as the first organic phase, which was sent to deacidification column. The first organic phase was deacidified to obtain a deacidified first organic phase and was stored in a large storage vessel.

The first aqueous phase from the separator was continuously collected and stored in a HDPE container.

The deacidified first organic phase was fractionally distilled to obtain a fraction comprising unreacted benzene, a fraction comprising LAB (500 g), and a fraction comprising HAB.

Experiment 2: Trans-Alkylation Reaction

The fraction comprising HAB obtained in Experiment 1 containing 12% linear alkyl benzene and 88% heavier alkyl benzene (containing dilakylbenzenes and oligomers) was used in the transalkylation step.

150 ml (133 gm) of the fraction comprising HAB obtained in Experiment 1 was mixed with 140 ml (117.2 gm) of benzene in a 400 ml autoclave equipped with an overhead stirrer. To the above mixture, 65.2 gm of the aqueous phase comprising first partially spent ionic liquid obtained from Experiment-1 was added. HAB was transalkylated with benzene ( . . . amount) by heating the resultant mass at 120° C. under stirring for 2 h to to obtain a second product mixture. After 2 hours, the reaction mass was cooled to 40° C. and was allowed to settle for 20 minutes to obtain a second biphasic mixture comprising a second organic phase comprising LAB and a second aqueous phase comprising the second partially spent ionic liquid.

The upper layer was analyzed by gas chromatography for heavier alkyl benzene content. The conversion of heavier alkyl benzene was 60%.

The layers were separated. The second organic phase was deacidified to obtain a deacidified second organic phase.

The deacidified second organic phase was fractionally distilled to obtain a fraction comprising a second portion of LAB (100 g) and a fraction comprising unreacted HAB.

The first portion of LAB (500 g) obtained in alkylation step was mixed with the second portion of LAB (100 g) obtained in transalkylation step to obtain LAB (600 g).

Technical Advancements

The present disclosure described herein above has several technical advantages including, but not limited to, the realization of:

a process for alkylation of benzene using a safe catalyst;

a process for alkylation of benzene using a catalyst that is easy to regenerate and recycle; and a process for alkylation of benzene that easily retrofits into the equipment for HF catalyzed alkylation of benzene.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the invention to achieve one or more of the desired objects or results. While certain embodiments of the inventions have been described, these embodiments have been presented by way of example only, and are not intended to limit the scope of the inventions. Variations or modifications to the formulation of this invention, within the scope of the invention, may occur to those skilled in the art upon reviewing the disclosure herein. Such variations or modifications are well within the spirit of this invention.

The numerical values given for various physical parameters, dimensions and quantities are only approximate values and it is envisaged that the values higher than the numerical value assigned to the physical parameters, dimensions and quantities fall within the scope of the invention unless there is a statement in the specification to the contrary.

While considerable emphasis has been placed herein on the specific features of the preferred embodiment, it will be appreciated that many additional features can be added and that many changes can be made in the preferred embodiment without departing from the principles of the disclosure. These and other changes in the preferred embodiment of the disclosure will be apparent to those skilled in the art from the disclosure herein, whereby it is to be distinctly understood that the foregoing descriptive matter is to be interpreted merely as illustrative of the disclosure and not as a limitation.

The invention claimed is:

1. A process for preparing linear alkyl benzene by alkylation of benzene, said process comprising the following steps:
   a) alkylating benzene with an alkylating agent in the presence of an ionic liquid to obtain a first product mixture;
   b) allowing the first product mixture to settle to obtain a first biphasic mixture comprising a first organic phase and a first aqueous phase, wherein the first organic phase comprises linear alkyl benzene (LAB), heavier alkyl benzene (HAB) and unreacted benzene, and the first aqueous phase comprises first partially spent ionic liquid;
   c) deacidifying the first organic phase to obtain a deacidified first organic phase;
   d) fractionally distilling the deacidified first organic phase to obtain a fraction comprising unreacted benzene, a fraction comprising LAB and a fraction comprising HAB;
   e) transalkylating the fraction comprising HAB with benzene in the presence of the ionic liquid at a temperature in the range of 70° C. to 120° C. to obtain a second product mixture;
   f) allowing the second product mixture to settle to obtain a second biphasic mixture comprising a second organic phase and a second aqueous phase; wherein the second organic phase comprises LAB and the second aqueous phase comprises second partially spent ionic liquid;
   g) deacidifying the second organic phase, and fractionally distilling the deacidified second organic phase to obtain a fraction comprising LAB and a fraction comprising unreacted HAB; and
   h) regenerating the first partially spent ionic liquid obtained in step (b) and/or and the second partially spent ionic liquid obtained in step (f), and reusing the regenerated ionic liquid in the steps of alkylating and/or transalkylating for at least 6 cycles of regeneration;
   wherein the ionic liquid used in alkylation step and transalkylation step is at least one selected from the group consisting of fresh ionic liquid, regenerated ionic liquid, the first partially spent ionic liquid and the second partially spent ionic liquid;
   wherein the step (h) of regeneration of partially spent ionic liquid involves the following sub-steps:
      i. mixing the first partially spent ionic liquid obtained in step (b) and/or the second partially spent ionic liquid obtained in step (f) with a fourth fluid medium and an alkali followed by stirring the resultant mixture to obtain a suspension comprising a solid phase and a liquid phase;
      ii. separating the solid phase from the suspension; and
      iii. mixing the separated solid phase with a metal halide to obtain regenerated ionic liquid;
   wherein the alkali is at least on selected from the group consisting of triethylamine, sodium carbonate, sodium bicarbonate, potassium carbonate, potassium bicarbonate, sodium hydroxide, and potassium hydroxide;
   wherein the separated solid is at least one basic component of ionic liquid selected from the group consisting of $NR_1R_2R_3$, $(NR_1R_2R_3)_j$, $M1Xj$, $M1OH$, and $BMIMX_i$; and the fourth fluid medium is at least one selected from the group consisting of ethyl acetate, water, and methyl acetate.

2. The process as claimed in claim 1, wherein the alkylating agent is at least one olefin selected from the group consisting of C10 to C14 olefins.

3. The process as claimed in claim 1, wherein the alkylating agent is a hydrocarbon mixture comprising paraffins and olefins, and the volume ratio of paraffins to olefins in the hydrocarbon mixture is in the range of 20:1 to 4:1.

4. The process as claimed in claim 1, wherein the mole ratio of benzene to the alkylating agent is in the range of 3:1 to 20:1.

5. The process as claimed in claim 1, wherein the alkylation step (a) is carried out in two stages, wherein the first stage comprises alkylating benzene with a first portion of the alkylating agent to obtain a first resultant mixture comprising unreacted benzene, and the second stage comprises alkylating the first resultant mixture comprising unreacted benzene with a second portion of the alkylating agent to obtain the first product mixture.

6. The process as claimed in claim 1, wherein the alkylation step is carried out at a temperature in the range of 5° C. to 150° C.

7. The process as claimed in claim 1, wherein the alkylation step is carried out at a pressure in the range of 1 atmosphere to 50 atmosphere.

8. The process as claimed in claim 1, wherein the volume ratio of the ionic liquid to benzene is in the range of 1:1000 to 1:10.

9. The process as claimed in claim 1, wherein the ionic liquid is a metal halide based ionic liquid obtained by mixing an acidic component with a basic component, wherein the acidic component is a metal halide and the basic component is at least one selected from the group consisting of $(NR_1R_2R_3)_i$ $M_1X_j$, $M_1(OH)_m$, $M_iX_j$, and $BMIMX_i$, wherein M 1 and M i are metals independently selected from the group consisting of Al, Fe, Zn, Cu, Ni, Ga, Ge and In;

'BMIM' represents 1-Butyl-3-methylimidazolium; and

Xj and X i are halogens independently selected from the group consisting of fluorine, chlorine, bromine and iodine.

10. The process as claimed in claim 1, wherein the ionic liquid is represented by formula (I).

$$[(NR_1R_2R_3)_iM_1]^{n+}[(M_2Y_k)_LX_j]^{n-} \quad \text{Formula (I)}$$

wherein, $NR_1R_2R_3$ represents an amine, wherein $R_1$, $R_2$ and $R_3$ are independently selected from the group consisting of alkyl, aryl and H;

$M_1$ and $M_2$ are metals independently selected from the group consisting of Al, Fe, Zn, Cu, Ni, Ga, Ge and In;

X and Y are halogens independently selected from the group consisting of fluorine, chlorine, bromine and iodine;

'n' represents 1 to 4, T represents 1 to 6, T represents 1 to 4, 'k' represents 1 to 4, represents 1 to 7, $M_1=M_2$ or $M_1 \neq M_2$, and X=Y or X≠Y, wherein the ionic liquid represented by Formula I is prepared by mixing a metal halide of formula M 2 Y k with a basic component of the formula $(NR_1R_2R_3)_i$, $M_1X_j$.

11. The process as claimed in claim 1, wherein the ionic liquid is represented by formula (III), $$[UM_iX_j]S \quad \text{Formula (III)}$$

wherein, 'U' represents urea; $M_iX_j$ represents metal halide, wherein M is at least one metal selected from the group consisting of Al, Fe, Zn, Ge, Cu, Ni, In, and Ga; and X is at least one halogen selected from the group consisting of fluorine, chlorine, bromine and iodine;

'i' represents 1 to 6, 'j' represents 1 to 6;

'S' represents a second fluid medium selected from the group consisting of benzene, and toluene;

wherein the weight % of the second fluid medium in the ionic liquid of formula III is in the range of 10 to 60%; and wherein the ionic liquid represented by Formula III is prepared by mixing a metal halide of formula $M_iX_j$ with urea as a basic component.

12. The process as claimed in claim 1, wherein the ionic liquid is represented by formula (IV), $$[BMIM][MX_iY_j)_k] \quad \text{Formula (IV)}$$

wherein, 'BMIM' represents 1-Butyl-3-methylimidazolium, M is at least one metal selected from the group consisting of Al, Fe, Ni, Cu, Zn, Ga, Ge, and In;

X and Y are halogens independently selected from the group consisting of chloride, bromide, fluoride and iodide;

'i' represents 1 to 4, 'j' represents 1 to 4, X=Y or X≠Y;

the ionic liquid of formula IV is optionally mixed with a third fluid medium selected from the group consisting of benzene, and toluene, wherein the weight % of the third fluid medium and the ionic liquid of formula IV is in the range of 10% to 40%; and wherein the ionic liquid represented by Formula IV is prepared by mixing the metal halide of formula $MY_j$ with the basic component of the formula $BMIMX_i$.

13. The process as claimed in claim 1, wherein the step (b) of separating the solid phase from the suspension comprises extracting the separated solid using a fifth fluid medium to obtain an extract; and removing the fifth fluid medium from the extract to obtain a residue comprising the solid phase; wherein the fifth fluid medium is dichloromethane.

14. The process as claimed in claim 1, wherein the step of regeneration of partially spent ionic liquid involves the following sub-steps:

a. mixing the first partially spent ionic liquid obtained in step (b) and the second partially spent ionic liquid obtained in step (f) with at least one sixth fluid medium and at least one coordinating agent to obtain a suspension comprising an adduct of the coordinating agent with the ionic liquid;

b. separating the adduct from the suspension; and c. thermally treating the separated adduct to obtain regenerated ionic liquid;

wherein the coordinating agent is at least one selected from the group consisting of secondary alcohol, aromatic alcohol, phenol and ketone; wherein the secondary alcohol is at least one selected from the group consisting of isopropanol and 2-butanol, preferably isopropanol; the aromatic alcohol is 1-phenylethanol; and the ketone is acetone; and wherein the molar ratio of the coordinating agent o the metal halide of the ionic liquid ranges from 1:1 to 1:18.

15. A process for preparing linear alkyl benzene by alkylation of benzene, said process comprising the following steps:

a) alkylating benzene with an alkylating agent in the presence of an ionic liquid to obtain a first product mixture;

b) allowing the first product mixture to settle to obtain a first biphasic mixture comprising a first organic phase and a first aqueous phase, wherein the first organic phase comprises linear alkyl benzene (LAB), heavier alkyl benzene (HAB) and unreacted benzene, and the first aqueous phase comprises first partially spent ionic liquid;

c) deacidifying the first organic phase to obtain a deacidified first organic phase;

d) fractionally distilling the deacidified first organic phase to obtain a fraction comprising unreacted benzene, a fraction comprising LAB and a fraction comprising HAB;

e) transalkylating the fraction comprising HAB with benzene in the presence of the ionic liquid at a temperature in the range of 70° C. to 120° C. to obtain a second product mixture;

f) allowing the second product mixture to settle to obtain a second biphasic mixture comprising a second organic phase and a second aqueous phase; wherein the second organic phase comprises LAB and the second aqueous phase comprises second partially spent ionic liquid;

g) deacidifying the second organic phase, and fractionally distilling the deacidified second organic phase to obtain a fraction comprising LAB and a fraction comprising unreacted HAB; and h) regenerating the first partially spent ionic liquid obtained in step (b) and/or and the second partially spent ionic liquid obtained in step (f), and reusing the regenerated ionic liquid in the steps of alkylating and/or transalkylating for at least 6 cycles of regeneration;

wherein the ionic liquid used in alkylation step and transalkylation step is at least one selected from the group consisting of fresh ionic liquid, regenerated ionic liquid, the first partially spent ionic liquid and the second partially spent ionic liquid;

wherein the ionic liquid is represented by formula (II), $$[(M_1)_p(M_2)_q(M_3)_r(OH)_m(X)_n(Y)_o \text{ (first fluid medium)}] \quad (II)$$

wherein, M 1, M 2 and M 3 are metals independently selected from the group consisting of Al, Fe, Ni, Cu, Zn, Ga, Ge, and In;

X and Y are halogens independently selected from the group consisting of fluorine, chlorine, bromine and iodine;

'p' represents 0 to 5, 'q' represents 0 to 5, 'r' represents 0 to 5, 'm' represents 10 to 420, 'n' represents 10 to 920, 'o' represents 10 to 420, X=Y or X≠Y, OH is hydroxyl group, wherein the first fluid medium is at least one selected from the group consisting of benzene, and toluene; wherein the weight % of the first fluid medium in the ionic liquid of formula II is in the range of 10% to 60%, wherein the ionic liquid represented by Formula II is prepared by mixing metal halides of formula $M_2(X)_n$ and $M_3(Y)_o$ with a basic component of the formula $M_1(OH)_m$.

* * * * *